(12) United States Patent
Carvalho et al.

(10) Patent No.: US 9,125,708 B2
(45) Date of Patent: Sep. 8, 2015

(54) MEDICAL IMPLANT AND METHOD OF IMPLANTATION

(75) Inventors: Paulo Malo Carvalho, Liboa (PT); Lars Jörneus, Frillesås (SE); Henrik Petersson, Göteborg (SE)

(73) Assignee: Nobel Biocare Services AG, Zurich-Flughafen (CH)

(*) Notice: Subject to any disclaimer, the term of this patent is extended or adjusted under 35 U.S.C. 154(b) by 163 days.

(21) Appl. No.: 13/003,260

(22) PCT Filed: Jul. 9, 2008

(86) PCT No.: PCT/EP2008/005585
§ 371 (c)(1),
(2), (4) Date: Mar. 31, 2011

(87) PCT Pub. No.: WO2010/003433
PCT Pub. Date: Jan. 14, 2010

(65) Prior Publication Data
US 2011/0183291 A1      Jul. 28, 2011

(51) Int. Cl.
*A61C 8/00* (2006.01)

(52) U.S. Cl.
CPC .............. *A61C 8/0018* (2013.01); *A61C 8/0034* (2013.01); *A61C 8/0022* (2013.01)

(58) Field of Classification Search
CPC ... A61C 8/0034; A61C 8/0018; A61C 8/0022
USPC ............ 433/172–175, 201.1, 167; 623/16.11, 623/17.18
See application file for complete search history.

(56) References Cited

U.S. PATENT DOCUMENTS

| 4,746,294 A | 5/1988 | Colombo et al. |
| 4,762,492 A * | 8/1988 | Nagai ........................... 433/174 |
| 4,964,801 A | 10/1990 | Kawahara et al. |

(Continued)

FOREIGN PATENT DOCUMENTS

| DE | 10236125 | 2/2004 |
| WO | WO/01/74412 | 10/2001 |

(Continued)

OTHER PUBLICATIONS

Ferrara et al., "Restoration of the Edentulous Maxilla: The Case for Zygomatic Implants," 2004, J Oral Maxillofac Surg 62:1418-1422.*

(Continued)

*Primary Examiner* — Cris L Rodriguez
*Assistant Examiner* — Mirayda A Aponte
(74) *Attorney, Agent, or Firm* — Knobbe Martens Olson & Bear LLP

(57) ABSTRACT

A medical implant and a method of implanting a medical implant are described. In some embodiments, the medical implant can include an apical bone anchoring portion for bone apposition, and an unthreaded coronal portion. The coronal portion can have a length ($L_2$) exceeding or equaling a length ($L_1$) of the apical portion. Further, in some embodiments, the apical portion has a maximum outer diameter ($D_1$) that is equal to or larger than a maximum outer diameter ($D_2$) of the coronal portion. In some embodiments of the method, an apical part of an implant is affixed in the zygomatic bone, and a coronal part is positioned outside the maxilla in the mucous membrane.

16 Claims, 6 Drawing Sheets

(56) References Cited

U.S. PATENT DOCUMENTS

| | | | |
|---|---|---|---|
| 5,201,736 A * | 4/1993 | Strauss | 606/285 |
| 5,269,686 A * | 12/1993 | James | 433/174 |
| 5,350,300 A * | 9/1994 | Gallais | 433/173 |
| 5,362,236 A | 11/1994 | Branemark | |
| 5,564,923 A * | 10/1996 | Grassi et al. | 433/173 |
| 5,564,926 A * | 10/1996 | Brånemark | 433/174 |
| 6,325,628 B1 * | 12/2001 | Morgan | 433/173 |
| 6,887,077 B2 * | 5/2005 | Porter et al. | 433/174 |
| 7,125,253 B2 * | 10/2006 | Kitamura et al. | 433/173 |
| 2005/0084822 A1 * | 4/2005 | Stucki-McCormick | 433/173 |
| 2005/0106534 A1 | 5/2005 | Gahlert | |
| 2005/0277090 A1 * | 12/2005 | Anderson et al. | 433/173 |
| 2006/0115791 A1 | 6/2006 | Carvalho | |
| 2006/0166169 A1 * | 7/2006 | Dawood | 433/174 |
| 2006/0246398 A1 * | 11/2006 | Groll et al. | 433/173 |

FOREIGN PATENT DOCUMENTS

| | | |
|---|---|---|
| WO | WO/03/003936 | 1/2003 |
| WO | WO/2005/027771 | 3/2005 |
| WO | WO/2005/079697 | 9/2005 |

OTHER PUBLICATIONS

Ferrara et al., "Restoration of the Edentulous Maxilla: The Case for the Zygomatic Implants", American Association of Oral and Maxillofacial Surfeons, 2004, http://www.cirugiafacial.cl/uploads/files/IR02.2004.pdf.*

PCT/EP2008/005585 International Search Report dated Apr. 16, 2009 issued in the name of Nobel Biocare Services AG in 3 pages.

Wennerberg, Ann et al., Design and Surface Characteristics of 13 Commercially Available Oral Implant Systems, JOMI, vol. 8, No. 6 pp. 622-633, (1993).

Stella et al. "Sinus Slot Technique for Simplification and Improved Orientation of Zygomaticus Dental Implants: A Technical Note". The International Journal for Oral & Maxillofacial Implants. vol. 15, No. 6, 2000. pp. 889-893.

* cited by examiner

मेDICAL IMPLANT AND METHOD OF
IMPLANTATION

PRIORITY INFORMATION

This application is a U.S. National Phase of International Application No. PCT/EP2008/005585, filed on Jul. 9, 2008, the entirety of which is hereby incorporated herein by reference.

BACKGROUND

1. Field of the Inventions

This application pertains in general to the field of medical implants and methods for implantation of such implants. In particular, certain embodiments relates to dental implants and methods for their implantation.

2. Description of the Related Art

Various types of medical implants are known, e.g. as anchoring elements that are intended to be implanted in patients' jaws. Upon implantation these anchoring elements support e.g. dental restorations via a connection interface.

Due to various reasons, such as diseases, bone quality may be poor in certain bone regions of a patient. In edentulous or partly edentulous patients jaw bone tissue may be highly resorbed. Therefore it may be difficult or impossible to satisfactorily anchor conventional medical implants in such damaged or resorbed bone tissue regions. For instance in the maxilla, i.e. the upper jaw, special elongate anchoring elements may be used that are anchored both in the maxilla and in the os zygomaticus, i.e. the zygomatic bone. Conventionally, the anchoring element is affixable by a double anchoring technique in the maxilla and the zygomatic bone. Between the maxilla and the zygomatic bone the anchoring elements extend through a cavity in the skull, the maxillary sinus cavity.

In U.S. Pat. No. 5,362,236 and U.S. Pat. No. 5,564,926 such an elongate anchoring element and a method of implanting the anchoring element are disclosed. The anchoring element has two generally cylindrical portions with different diameters. A threaded apical end portion of the anchoring element has the smaller diameter thereof, and is intended to be positioned in the zygomatic bone. A threaded coronal portion of the anchoring element has the larger diameter thereof, and is intended to be positioned in the maxilla. The anchoring element is implanted by drilling two aligned bores in the bone tissue. The apical, smaller diameter, portion of the anchoring element is passed through the larger diameter bore in the maxilla and is threaded into the smaller diameter bore in the zygomatic bone. While self-threading by the apical, smaller diameter, portion takes place in the second bore, the larger diameter portion is self-threaded in the first, larger diameter, bore in the maxilla. Thus, the anchoring element may be reliably double anchored when applied.

However, both anchoring elements and methods, such as disclosed in U.S. Pat. No. 5,362,236 and U.S. Pat. No. 5,564,926 may be further improved or provided with alternatives. An alternative anchoring element is disclosed in WO2005/079697. The anchoring element comprises a first fixation portion, disposed at the apex, a second fixation portion, disposed at the basis of the anchoring element, and an intermediate portion in between the first and second fixation portion. For instance, working inside and from inside the maxillary sinus may be difficult due to limited visibility, space etc. Access hole in the maxillary bone is sometimes opened towards the maxillary sinus cavity, in order to gain a field of sight into the maxillary sinus cavity. However, this may be both cumbersome and imply healing complications for the patient.

Thus, there is a need for an improved medical implant and/or medical method for implanting a medical implant. Hence, an improved medical implant and/or medical method for implanting a medical implant would be advantageous. In particular a medical implant and/or medical method for implanting a medical implant allowing reliable anchoring in bone tissue; increased surgical flexibility; improved surgical control, e.g. by improved visible feedback of the medical procedure; and/or cost-effectiveness, e.g. by reduced surgery time, patient recovery time, potential side effects; etc. would be advantageous.

SUMMARY

Accordingly, embodiments of the present inventions preferably seek to mitigate, alleviate or eliminate one or more deficiencies, disadvantages or issues in the art, such as the above-identified, singly or in any combination by providing a medical implant and a method of implanting a medical implant according to the appended patent claims.

According to some embodiments, a medical implant is provided. The medical implant is an elongate medical implant for fixation in a patient. The implant comprises an apical bone anchoring portion for bone apposition, and a non-threaded coronal portion, wherein the coronal portion has a length exceeding a length of the apical portion, and wherein the apical portion has a maximum outer diameter that is equal to or larger than a maximum outer diameter of the coronal portion.

According to some embodiments, a method of implanting a medical implant in a patient in a medical procedure is provided. The method comprises creating a first recess in a facial surface of bone tissue of a maxilla of the patient; creating an anchoring bore externally in facial skull bone tissue at a distance from a location of the first recess in the facial surface of the maxilla; and implanting a medical implant with an apical anchoring portion thereof in the anchoring bore, and positioning a non-threaded coronal part of the medical implant adjacent the first recess.

The medical implant and the method enables a more beneficial position and location of the implant interface against the bridge or tooth/teeth replacement. This in turn provides for use of a less voluminous replacement. Furthermore, the implant describes an alternative path from the zygomatic bone, which does not occupy so much space in the oral cavity. This is considered advantageous for esthetic reasons and provides for more space for the tongue. The beneficial position of the inventive implant, when attached to the zygomatic bone in accordance with the method, in relation to the dental restoration allows for a more aligned load transfer, which may alleviate the surrounding body parts as well. Further embodiments are defined in the dependent claims, wherein features for the second and subsequent embodiments are as for the first aspect mutatis mutandis.

Some embodiments provide for a fixture of a dental restoration that provides for improved anchoring.

Some embodiments also provide for an improved medical implant that provides reliable anchoring in skull bone tissue and a connection interface at an alveolar ridge of a maxilla.

Some embodiments provide for a medical implant that facilitates implantation thereof.

Some embodiments provide for a method of implanting a medical implant, wherein visibility of the implantation is improved.

Thus, some embodiments provide for improved precision and safety of implantation.

Some embodiments provide for a medical procedure of implanting a medical implant that is more securely and less complicated to perform for a surgeon. Some embodiments provide for increased surgical flexibility. Some embodiments provide for improved surgical control, e.g. by improved visible feedback of the medical procedure. Some embodiments provide for cost-effectiveness, e.g. by reduced surgery time, patient recovery time, potential side effects, etc.

It should be emphasized that the term "comprises/comprising" when used in this specification is taken to specify the presence of stated features, integers, steps or components but does not preclude the presence or addition of one or more other features, integers, steps, components or groups thereof.

BRIEF DESCRIPTION OF THE DRAWINGS

These and other aspects, features and advantages of which some embodiments are capable of will be apparent and elucidated from the following description of embodiments, reference being made to the accompanying drawings, in which.

DESCRIPTION OF EMBODIMENTS

Figures 1A, 1B:
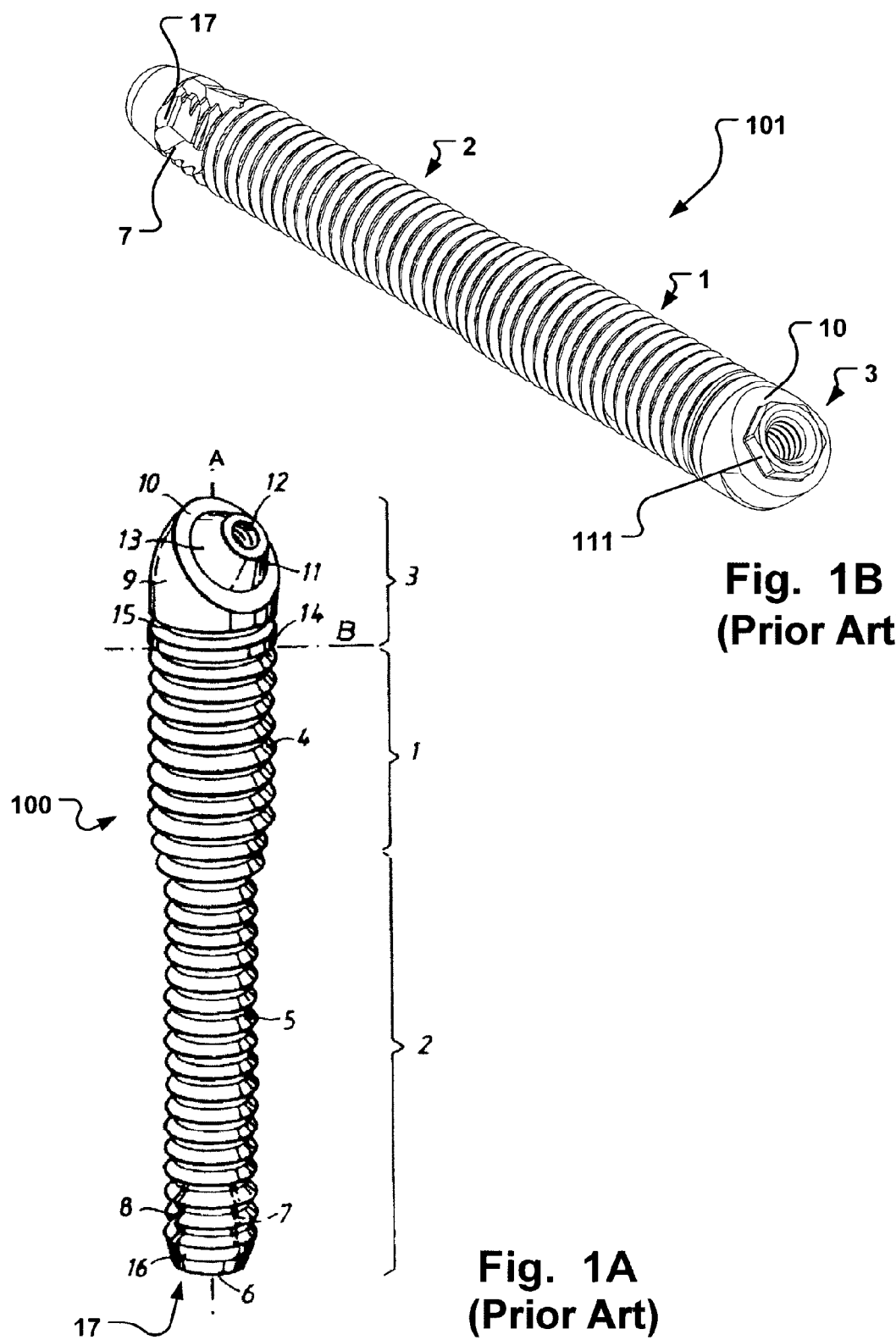
FIG. 1A is a perspective view of a prior art medical implant.
FIG. 1B is a perspective view of a prior art medical implant.

Specific embodiments will now be described with reference to the accompanying drawings. Some embodiments may, however, be embodied in many different forms and should not be construed as limited to the embodiments set forth herein; rather, these embodiments are provided so that this disclosure will be thorough and complete, and will fully convey the scope of the inventions to those skilled in the art. The terminology used in the detailed description of the embodiments illustrated in the accompanying drawings is not intended to be limiting. In the drawings, like numbers refer to like elements.

The following description focuses on an embodiment applicable to a dental implant for anchoring in skull bone, such as the zygomatic bone. Such anchoring dental implants are also referred to as fixtures. However, it will be appreciated that the embodiments are not limited to this application.

The medical implants 100, 101 shown in FIG. 1A and FIG. 1B comprise two longitudinally adjoining cylinder-shaped segments. FIG. 1A corresponds to FIG. 1 of U.S. Pat. No. 5,362,236 and U.S. Pat. No. 5,564,926 of the same proprietor as the applicant of the present application, which hereby are incorporated in their entirety for all purposes. The implant is essentially composed of two cylindrical segments bordering each other and being in alignment, wherein the first, coronal segment 1 has a diameter larger than that of the second, apical segment 2.

The outside of the implant is threaded, except for a mounting portion extending from the coronal end of the implant and connected to the cylindrical coronal segment 1. The outer threads comprise first threads 4 on the coronal cylindrical segment 1 and second threads 5 on the apical cylindrical segment 2. The pitch is the same for both threads 4, 5 merging at the border zone between the cylindrical segments. The inner diameter of first threads 4 is larger than the outer diameter of the second threads 5. Threads 4, 5 are self-tapping.

A symmetrically centered bore 17 extends from the apical end 6 and has an extension corresponding to about half the length of the apical segment 2. Two through slits 7, 8 arranged symmetrically in segment 2 and in its longitudinal direction extend from a plane perpendicular to the central axis near the apical end 6. Slits 7, 8 establish communication between the outside of apical segment 2 and the symmetrically centered bore 17 arranged therein for transport of bone material removed by ablation. The outside of apical segment 2 is beveled (beveling 16) towards apical end 6.

The mounting section 3 is contained within a cylindrical chamber with a diameter corresponding to the outer diameter of coronal cylindrical segment 1. The mounting segment 3 comprises a base portion 9 having the form of a cylindrical body dissected by a plane at an angle of 45 DEG in respect of the cylinder axis. The circular basis of base portion 9 is connected to the coronal end of the coronal cylindrical segment 1 with which it merges. Nearest to the coronal cylindrical segment 1 base portion 9 has an annular flange 14 to which an annular groove 15 connects in direction of the coronal end. End face 10 of base portion 9 is defined by a dissecting plane and, at its coronal zone, smoothly rounded joins the cylinder mantle of base section 9, the beading decreasing gradually towards the apical portion of the base section. Because of the beveling the profile of end face 10 is substantially circular. In its center end face 10 has a bore 12 running at an angle of 45 degrees in respect of longitudinal axis A of the implant 100. At bore 12 base section 9 is extended under formation of a frustum of a cone 11 tapering in direction away from base section 9. Mantle surface 13 of the cone frustum 11 and the annular end face 10 are designed for sealing abutment of a dental prosthesis or bridge (not shown) that can be mounted on the base portion by screw means.

The implant 101 shown in FIG. 1B differs from the implant 100 of FIG. 1A in that the connection interface comprises a hexagonal unit 111 instead of the frusto conical part 11.

Figure 2A:
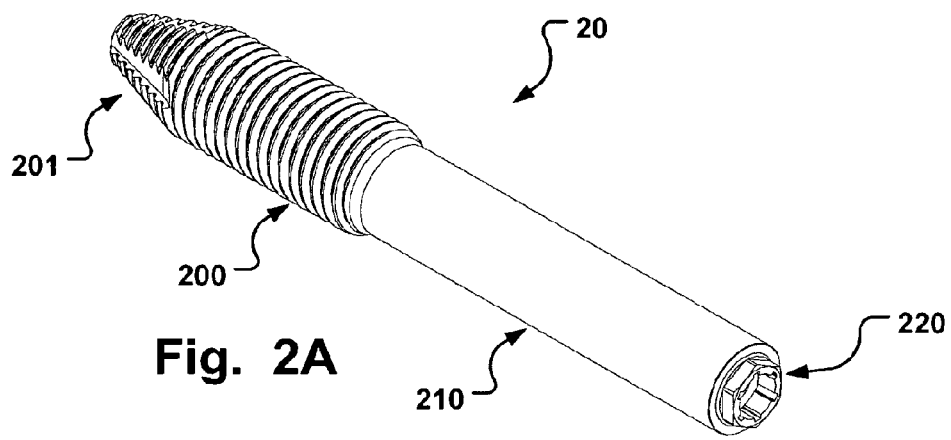
FIG. 2A is a perspective view of an embodiment of a medical implant.
Figure 2B:
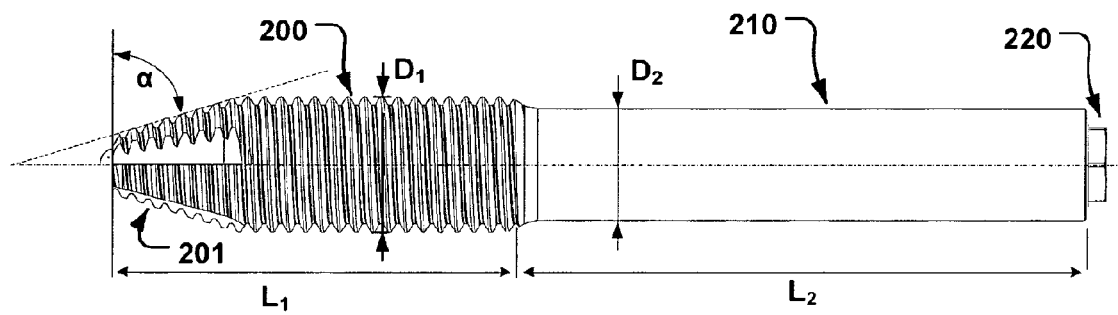
FIG. 2B is a lateral view of the implant of FIG. 2A.

FIGS. 2A and 2B illustrate embodiments of an elongate medical implant 20. The elongate medical implant 20 is devised for fixation in bone tissue in a patient.

The implant 20 comprises a helically threaded apical bone anchoring portion 200 for bone apposition. A tapered top portion 201 is provided at the apical portion 200. The top portion is tapered towards an apical end of the implant 20. The tapered top portion 201 of the implant 20 is tapered with a tapering angle in the range between 25 to 75 degrees. Thanks to the tapered top portion, entry into a bore is readily found upon implantation. The implant 20 is homing and self-centering in the bore. This is particularly advantageous, when the bore is partly hidden or obscured. Thus, the tapered top portion 201 facilitates insertion of the apical end of implant 20 into a bore.

The apical portion 200 may be cylindrical except for the tapered top portion 201. The apical portion 200 may also be slightly tapering towards the top portion 201 for improved primary stability of the implant upon implantation. A diameter of the apical end by the tapered top portion 201 is less than half of the maximum outer diameter of the apical portion ($D_1$).

Alternatively, the apical portion 200 may be conical or at least partly conical, tapering towards the tapered portion 201. Tapered portion 201 may in some embodiments comprise a bevel at the apical end.

The thread of the helically threaded apical bone anchoring portion 201 is, upon implantation in bone tissue, used to convert between rotational and linear movement. That means by rotating the implant 20 the implant 20 is screwed into the bore in longitudinal direction thereof. The peak and valley structure of the thread provides a primary stability of the implant 20 in the bone tissue.

In other embodiments the implant may alternatively, or in addition, comprise other bone anchoring structures than a helical thread. The apical portion may be provided with other bone engagement interfaces. The apical portion may for instance be devised to provide fixation by frictional engagement in the bore. Fixation of the apical portion to bone tissue may also be provided by structures providing pressure towards the appositioned bone tissue, similar like a plug or peg. Such structures may be annular ribs. A trade off between implantation time and primary stability, as well as long-term osseointegration of the implant may be made.

The implant 20 further comprises an unthreaded coronal portion 210. Unthreaded means that no thread is present along the coronal portion 210. An alternative term to unthreaded in this context is non-threaded, i.e. there is no peak and valley structure of a thread provided at the coronal portion 210. The coronal portion 210 is substantially smooth on a macro level. The macro roughness (explained below) of the coronal portion 210 is substantially lower than that of the anchoring portion.

This provides for a portion of the implant 20 that is arranged to not irritate or damage appositioned soft tissue, such as gingiva, including embedded muscles, blood vessels, or nerves. However, the surface of the non-threaded coronal portion may be provided with a surface roughness on a micro level, as is elucidated below.

In other embodiments the term unthreaded comprises that the substantially smooth extension of the coronal portion 210 is free of bone anchoring structures. The coronal portion 210 is free of projections that may affect appositioned soft tissue.

Conventional anchoring elements, such as disclosed in U.S. Pat. No. 5,362,236 and U.S. Pat. No. 5,564,926, may comprise threaded portions that are appositioned to tissue when applied. However, threaded portions of the anchoring element may irritate or damage the tissue, e.g. in the maxillary sinus cavity. Also, tissue from the maxillary sinus may be caught by the thread of the apical part of the anchoring element, which might lead to impaired osseointegration and secondary stability in the zygomatic bone and eventually loosening of the anchored implant.

Some embodiments provide for improved soft tissue apposition. Thanks to the unthreaded portion 210, a normal physiological function of the soft tissue is provided when appositioned to the implant at that portion of the dental implant. Conditions, such as soft tissue irritation or damage, catarrh or irritation of the mucous membrane are effectively prevented. A prophylactic treatment is comprised in this prevention.

The coronal portion 210 may have a surface with a coarse micro roughness, wherein the coronal portion 210 is adapted to provide a tissue friendly portion.

The outer surface of the implant 20, hereinafter also called "surface" for the sake of simplicity, may have a topography with a macro roughness, e.g. in the form of one or several threads at the anchoring portion 200 in order to mechanically anchor the medical implant in surrounding bone tissue. Topography is amongst others defined as the study or detailed description of the surface features of a region of an object, here of the medical implant. The medical implant has an outer surface and the geometry thereof follows a defined topography both on a macro scale and a micro scale.

Figure 3A:
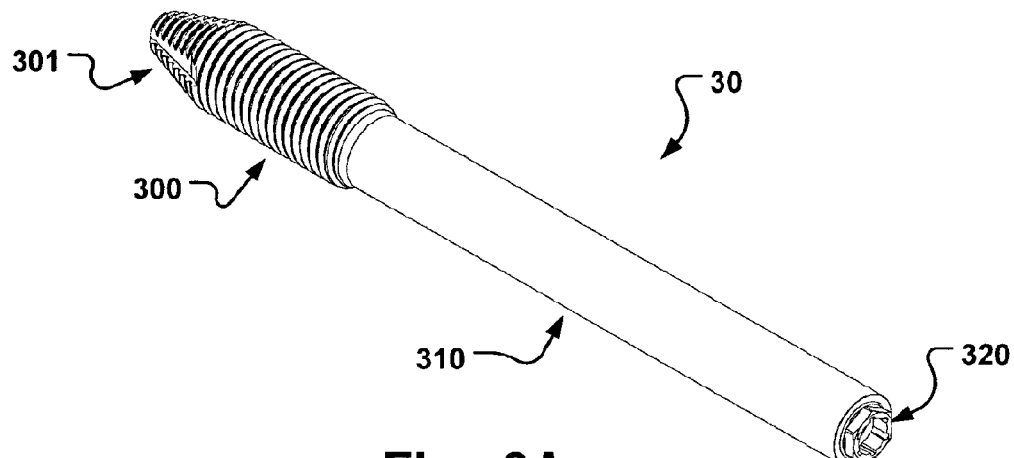
FIG. 3A is a perspective view of another embodiment of a medical implant.
Figure 3B:
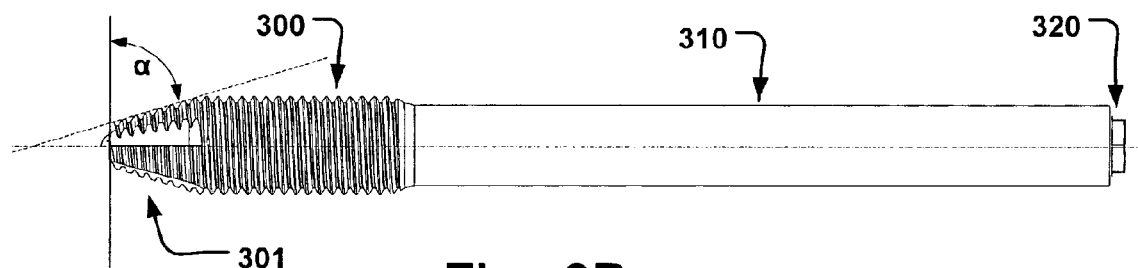
FIG. 3B is a lateral view of the implant of FIG. 3A.
Figure 3C:
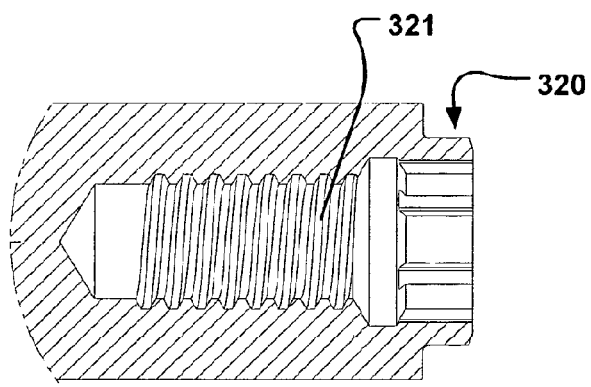
FIG. 3C shows a coronal end portion of the implant of FIGS. 3A-3B in cross section.

The macro roughness defines the outer geometry of the medical implant. In FIGS. 2A and 3A, the macro roughness is illustrated in the form of a threaded part of the medical implant 20 or 30. Additionally, the macro roughness of the threaded outer surface 40 may in itself have a surface roughness, for instance defined as a porosity of the surface, but this is referred to below as micro roughness. The macro roughness of the surface lies for instance for a medical implant in the mm range, wherein the macro roughness may further be subdivided into finer structures, such as grooves on threaded portions, or non-threaded portions in the sub mm range.

Furthermore, the outer surface of the medical implant may have a micro roughness in the μm range. The micro roughness defines the topography of the surface of embodiments of medical implants in the present context. In contrast, the above-described macro roughness is defined by the outer contour of the medical implant.

For instance, in case the implant 20 is a ceramic implant, the outer surface topography may be machined and densely sintered without a processed outer surface thereof, i.e. after sintering the ceramic medical implant, has a very fine micro roughness. Coronal portion 210 may advantageously have such a surface. However, such a smooth outer surface has disadvantageous properties with regard to osseointegration of the medical implant. Therefore, the anchoring portion may be provided with a more coarse or rough outer surface having an increased micro roughness compared to the untreated sintered outer surface, which improves osseointegration thereof. Such a coarse or rough outer surface may for instance be provided in the form of a porous, rough surface layer, having an outer surface roughness, for instance with a Ra value (explained below) in the μm range. For example, in WO 2005/027771, of the same applicant as the present application, which is incorporated herein by reference in its entirety, discloses a densely sintered ceramic medical implant having a ceramic layer arranged thereon. The ceramic layer, and thus an outer surface of the dental implant, is provided with a surface that has a porosity, which is larger or has more pores than in the underlying densely sintered ceramic material. In this manner, a ceramic medical implant is provided that fulfills the requirement of mechanical strength, and a considerable improvement of osseointegration is achieved. At the same time advantageous properties are achieved at the portion having a fine micro roughness at the coronal portion 210. Alternatively, the outer micro roughness of a ceramic medical implant may be provided on a ceramic substrate thereof by modifying the sintered outer surface, e.g. by chemical or mechanical abrasion methods, as for instance disclosed in US-A1-2005/0106534.

The medical implant 20 may be manufactured of other biocompatible materials, such as titanium oxide. In this case, the implant may be provided with a desired surface roughness. For instance the TiUnite® surface may be provided, as disclosed in WO0174412 or WO03003936 of same applicant as the present application, which are hereby incorporated in their entirety by reference for all purposes. The TiUnite® surface has a relatively high surface roughness and porosity.

Medical implants having such a suitable surface roughness reach immediately upon implantation a primary stability in bone tissue by the macro roughness, i.e. the macro structure of e.g. threads of the implant. The medical implant then osseointegrates with the surrounding bone tissue within a healing time of about 3 to 4 months, so that a secondary stability is provided, i.e. a permanent bond between the threaded anchoring part 200 of the medical implant screwed into the bone tissue and the bone tissue is provided. However during a certain time following the implantation, the total stability of the medical implant in the bone tissue decreases to a certain stability that is lower than the initial stability, i.e. the stability of the medical implant shows a stability dip after implantation. Then bone growth accelerates and osseointegration is achieved. Pores of the rough surface, into which the bone tissue is growing firmly, provide the secondary stability. In addition, also a mucous membrane may advantageously be in apposition to a surface having a coarse micro roughness, but a fine macro roughness.

A measure for surface roughness is parameters, such as Ra value (mean roughness), Rt value (maximum roughness), Sa value etc. The mean or average roughness (Ra) is defined as the average of absolute distance values of a number of measurements across a' surface of interest. Sa is the equivalent amplitude parameter on a 3D or areal basis.

Roughness measurements may for instance be performed according to procedures as determined in international standards. However, measurements in accordance with such international ISO standards may prove difficult to implement on dental implants, e.g. due to the small surfaces thereof.

Attempts have been made to define and measure surface roughness of prior art dental abutment and dental implants (see e.g., Wennerberg, Ann et al., Design and Surface Characteristics of 13 Commercially Available Oral Implant Systems, JOMI, Vol. 8, No. 6 pages 622-633, (1993), which hereby is incorporated by reference in its entirety). The Wennerberg article defines two surface roughness parameters: (i) Rt, which is the maximum peak to valley height of the profile of the surface (see page 623) and (ii) Ra, which is the mean value of the peak to valley distance.

Using the Wennerberg definitions, smooth machined and/or polished surface of implants have a Rt of approximately 10 microns or less and a Ra of approximately 0.6 microns or less.

The coronal portion 210 has a length $L_2$ exceeding a length $L_1$ of the apical portion 200. The apical portion 200 has a maximum outer diameter $D_1$ that is larger than a maximum outer diameter $D_2$ of the coronal portion 210. In a specific embodiment $D_1$ is equal to $D_2$.

The apical bone-anchoring portion 200 is devised for apposition to a zygomatic bone of the patient, as will be illustrated below.

The coronal portion 210 is at least partly devised for apposition to soft tissue, including gingiva and muscle tissue, of the cheek exterior of the maxilla. In an embodiment the coronal portion 210 is cylindrical along its entire length.

The coronal portion 210 may be devised for partial apposition to bone tissue and partial apposition to non-bone tissue. For instance the radial portion of the coronal portion oriented towards the maxilla upon implantation may be appositioned to the maxilla. As the implant 20 will be positioned outside of the maxilla, the outer radial part of the coronal portion 210 oriented away from the maxilla, towards the soft tissue may be devised for radial apposition to this soft tissue.

In embodiments the coronal portion 210 has a diameter $D_2$ that is smaller than an inner diameter of a thread of the apical portion 200 at the maximum outer diameter thereof, $D_1$.

As $D_2$ is smaller than $D_1$, a plurality of implants may be positioned with their coronal ends close to each other. Thus, stability of a dental restoration may be improved in that a plurality of implants fits in the narrow space at hand for this.

In embodiments, the coronal portion may be rotationally asymmetrical (not shown). This provides for improved anatomical flexibility when positioning the implant.

In practical embodiments the dental implant, as shown in FIGS. 2A-2C and 3A-3C may have the following approximate ranges and/or values of length and diameter thereof:
Total length ($L_1+L_2$): 30 mm to 55 mm
$L_1$ typically 15 mm
$L_2$: 15 to 40 mm
Ratio ($L_1/(L_1+L_2)$): approx 0,25 to 0,50
Ratio ($L_1/L_2$)): approx 0,35 to 1.0
$D_2$: is typically smaller than the diameter of the valleys of the threads or other grooves at the apical portion 200
Ratio ($D_1/D_2$)): 0,5 to 0,95

In embodiments, a ratio of the length of the apical portion (L1) to the length of the coronal portion ($L_2$) is in the range of 0,2 to 0,5.

The total length of the implant is the length of the apical portion plus the length of the coronal portion thereof. Any except further portions, e.g. protruding from the coronal portion are not included in the total length. Further protruding portions may for instance be mounting portions extending from a coronal end of the implant.

Conventionally, anchoring elements, such as disclosed in U.S. Pat. No. 5,362,236 and U.S. Pat. No. 5,564,926, have a bore having internal threads formed about an axis that is tilted with respect to a common axis for the cylindrical segments. External threads on prosthesis threadably engage the internal threads to secure such prosthesis to the anchoring element. However, due to the tilting angle, the mounting process may be cumbersome.

Figure 4A:
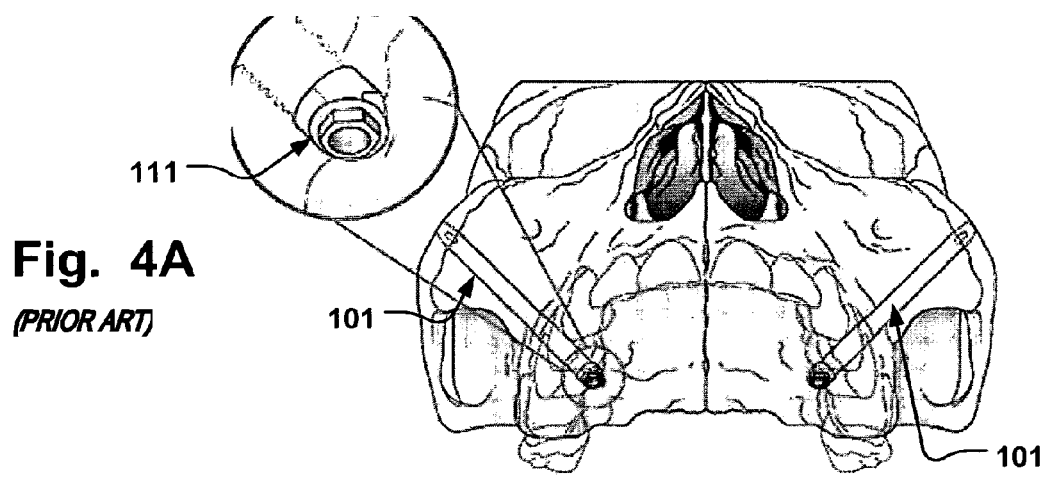
FIG. 4A is a view illustrating a conventional medical implantation procedure via the sinus cavity.
Figure 4B:
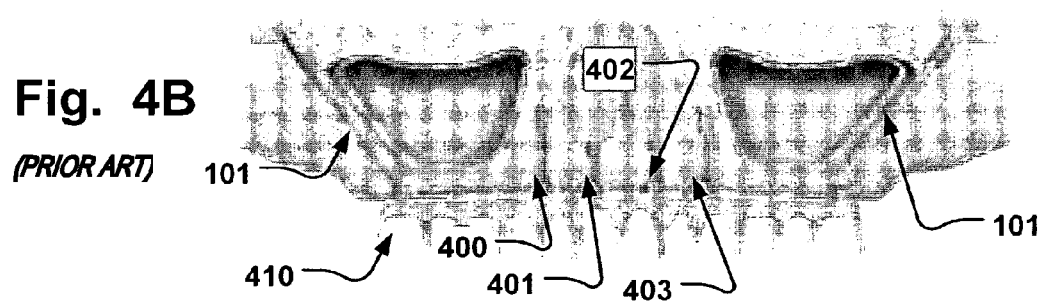
FIG. 4B is another view illustrating the conventional medical implantation procedure via the sinus cavity.
Figure 4C:
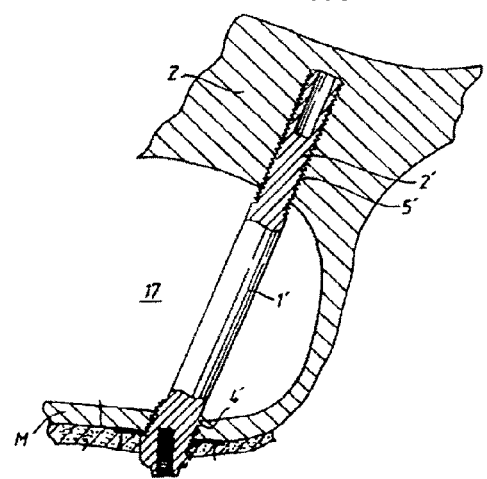
FIG. 4C is yet another view illustrating the conventional medical implantation procedure via the sinus cavity.

Traditionally, the conventional zygoma implants have their coronal end positioned at a distance from the alveolar ridge in a palatal direction, i.e. towards the inside of the oral cavity, such as shown in FIG. 4A, 4B or 4C. Thus, it may be difficult to provide a dental restoration at an anatomically correct position, as a distance from the coronal end of the zygoma implant to the position of the original alveolar ridge of the maxilla has to be bridged.

However, according to some embodiments, these issues are solved. A connection interface of a medical implant may be provided close to or at the alveolar ridge of the maxilla.

In more detail, the implant 20 moreover comprises a connection interface 220 for attachment of an abutment and/or a dental restoration, such as a tooth prosthesis or a bridge.

The connection interface 220 may comprise an inner helical thread at the coronal end of the implant 20 that is arranged substantially in direction of the longitudinal direction of the medical implant.

Conventional implants, such as shown in FIGS. 1A and 1B have a bore 12 running at an angle of e.g. 45 degrees in respect of longitudinal axis of the implant 100. The bore 12 defines the orientation of a connection interface for receiving an abutment carrying a dental restoration. The orientation of the bore 12, due to the angular orientation, is dependent on the rotational position of the implant upon implantation. Therefore, care has to be taken that the implant is screwed into a defined position towards an ideal occlusion plane.

Figure 2C:
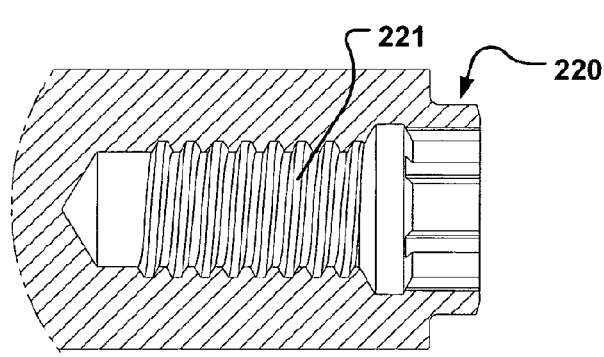
FIG. 2C shows a coronal end portion of the implant of FIGS. 2A-2B in cross section.

As shown in FIG. 2C, the threaded internal bore 221 of the connection interface 220 of the embodiment is oriented substantially in line with the longitudinal axis of implant 20. Thus an abutment connection interface is arranged substantially perpendicular to a longitudinal direction of the medical implant 20. Mounting of an abutment is thus advantageously facilitated, irrespectively of the rotational orientation of the implant upon implantation. The abutment may have a second connection interface that is angled in relation to the longitudinal axis of the implant 20, e.g. for attachment of a bridge, tooth prosthesis or similar dental restoration.

The implant 20 may be produced in a single monolithic piece. The implant 20 may alternatively be split in at least two interconnectable parts. For instance a connection interface may be provided between the apical and the coronal portion.

An application of implants 20, 30 will now be described with reference to a surgical method.

FIGS. 4A, 4B, and 4C are views illustrating a conventional medical procedure for implantation of a medical implant by double anchoring via the sinus cavity. Anchoring elements, such as described above with reference to FIG. 1A and FIG. 1B, have two portions with different diameters. The threaded apical end portion 2' of the anchoring element 1' has the smaller diameter thereof, and is intended to be positioned interiorly in the zygomatic bone Z. The threaded coronal portion 4' of the anchoring element 1' has the larger diameter thereof, and is intended to be positioned in the palatal region of the maxilla M. The anchoring element 1' is implanted by drilling two aligned bores in the bone tissues. A first bore, having a diameter suitable for anchoring the coronal portion, is drilled through the maxilla M. Drilling is continued through the maxillary sinus cavity 17 in the skull. Subsequently a second bore 5', having an appropriate diameter for anchoring the apical portion of the anchoring element, is drilled in the zygomatic bone Z from inside the maxillary sinus 17. The apical, smaller diameter, portion of the anchoring element is passed into the bore in the maxilla M and is threaded into the bore in the zygomatic bone Z. While self-threading by the apical, smaller diameter, portion takes place in the second bore, the larger diameter portion is self-threaded in the first bore in the maxilla. Thus, the anchoring element is double anchored. In FIG. 4B a dental bridge 410 is shown affixed to a plurality of implants 101 and 400, 401, 402, 403.

However, this conventional method has some drawbacks, as described above. In contrast to this conventional method, an improved method is provided. In an embodiment of the method, a first recess is made in the exterior bone surface of the maxilla, which is oriented towards the facial side of the maxilla, i.e. outside of the oral cavity. Removing bone tissue from the maxilla surgically creates the first recess. The first recess is made to provide a passage for the coronal portion of an anchoring element on the outside of the maxilla towards the alveolar crest thereof. The first recess does usually not extend into the maxillary sinus cavity and a remaining amount of bone tissue underlying the first recess is kept. The first recess commonly has a longitudinal extension oriented towards the exterior of a bone tissue at the zygomatic bone located on the same side of the skull as the first recess. Along its longitudinal extension, the first recess may be provided as a guide channel for a tool when creating an anchoring bore at the zygomatic bone. For instance a drill may be guided by the first recess towards an entry site of the anchoring bore when drilling a bore in the zygomatic bone. Thus, the longitudinal extension of the first recess in the outer surface of the maxilla is aligned with the longitudinal extension of the anchoring bore in the zygomatic bone. Creating the anchoring bore, such as by a drilling operation in accordance with some embodiments, may be made under good visibility of the surgical working area. Subsequent implantation of a medical implant in the anchoring bore is made. The medical implant, when thus applied, extends from its apical end in the anchoring bore to its coronal portion at the first recess towards the alveolar crest of the maxilla.

Figure 5A:
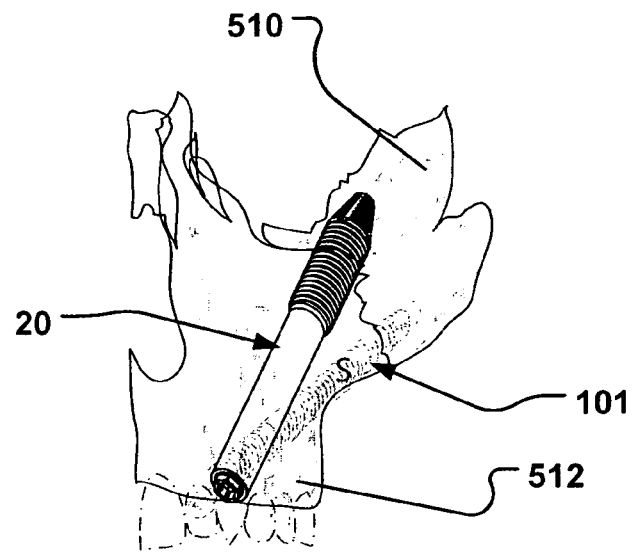
FIG. 5A is a frontal view illustrating implanting of a medical implant
Figure 5B:
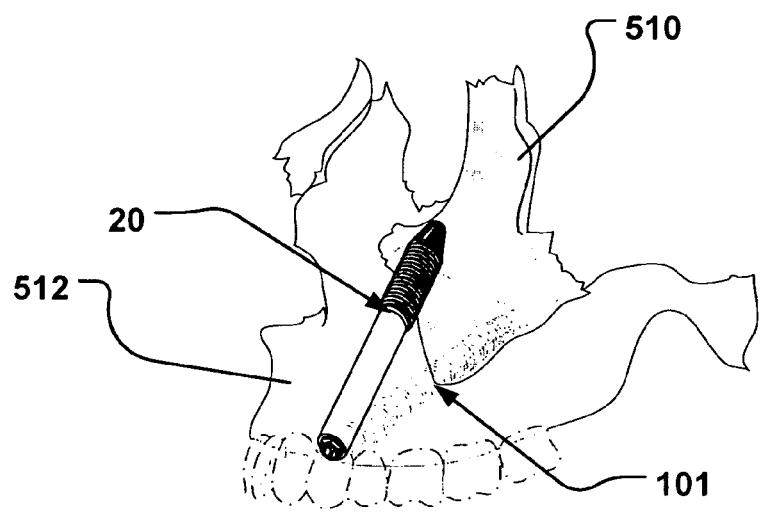
FIG. 5B is a lateral view illustrating implanting of a medical implant.
Figure 6:
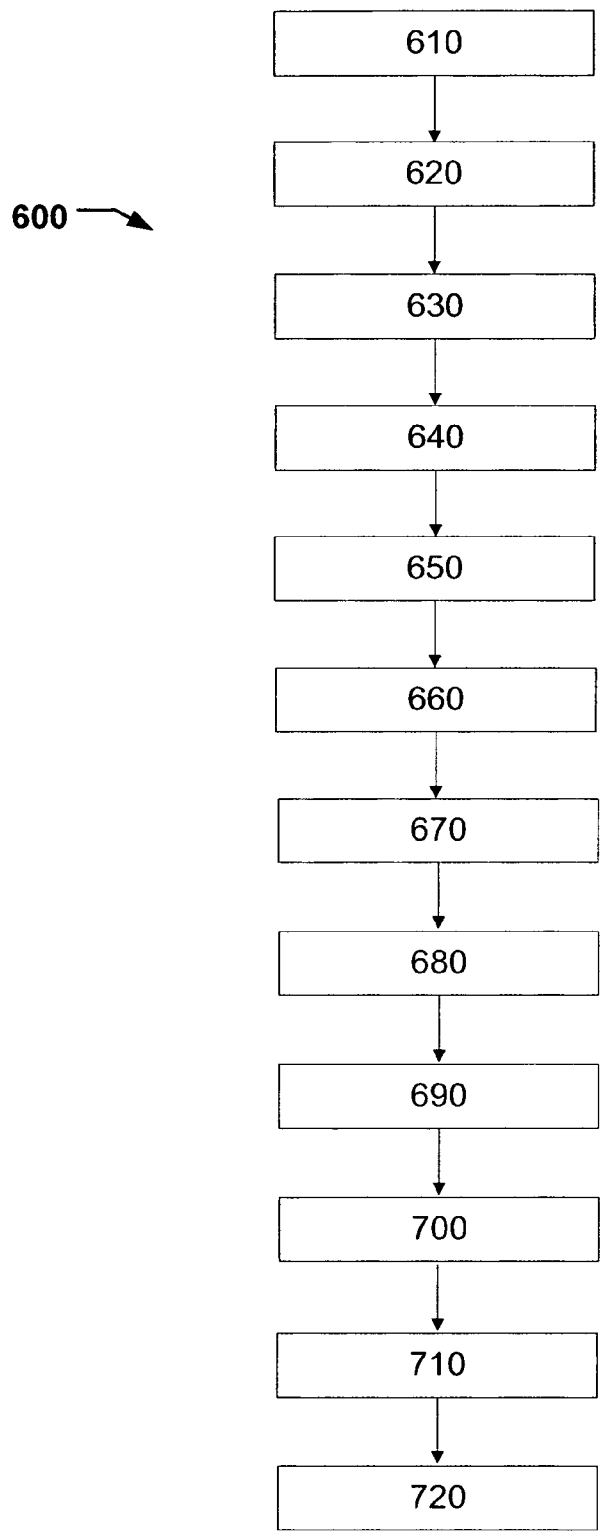
FIG. 6 is a flow chart illustrating a medical procedure of an embodiment.

Further embodiments of this method of implanting a medical implant in a patient will now be described. A specific embodiment will be elucidated further below with reference to FIGS. 5A, 5B and FIG. 6. FIG. 5A is a frontal view illustrating a medical implant 20 implanted extra maxillary. FIG. 5B is a lateral view illustrating the same situation. In addition, a conventional implant 101 is indicated, purely for illustrative purposes, in order to illustrate the difference between the present extra maxillary method and the conventional maxillary sinus cavity crossing method. For illustrative purposes the conventional implant is disclosed as attached for interconnecting with a bridge or similar at substantially the same location in the mouth as the inventive implant. This illustration discloses that the apical portions in such hypothetical case, end up at a very different locations. Since, the bone quality of the anchoring bone is decisive for how and where the implant can be affixed it would probably have been more correct to illustrate the different resulting positions of the coronal end portion of the respective implants instead. However, this situation is not illustrated and needs to be imagined. It is not considered difficult to understand, with hindsight, that there is a risk for the implant of the conventional type and hence applied by conventional methods to occupy more space by the palate cavity than is needed by shifting to the herein claimed technique.

In the present medical procedure, a medical implant is implanted in a patient. The medical procedure comprises creating a first recess in a facial surface of bone tissue of a maxilla of the patient; creating an anchoring bore externally in facial skull bone tissue at a distance from a location of the first recess in the facial surface of the maxilla; and implanting a medical implant with an apical anchoring portion thereof in the anchoring bore, and positioning a non-threaded coronal part of the medical implant adjacent the first recess.

The skull is normally made up of a number of skull bones. For instance the adult human skull comprises twenty-two bones. Except for the mandible, i.e. the lower jaw, all of the skull bones are joined together by sutures, semirigid articulations formed by bony ossification, whereby the presence of Sharpey's fibres permits a little flexibility between the skull bones. In embodiments of the method, the facial skull bone tissue is comprised in the zygomatic process at the zygomatic bone 510. The zygomatic process is a protrusion from the rest of the skull. Most of it belongs to the zygomatic bone, but there are other bones contributing to it too, namely the frontal bone, maxilla 512 and temporal bone.

When creating the anchoring bore, caution has to be made not to injure any anatomical sensitive structures, like nerves or vessels, e.g. passing through foramen in the maxilla or zygomatic bone.

The method may comprise embedding the coronal part of the medical implant under gingival tissue, once the anchoring in the anchoring bore is made. The method may comprise embedding the coronal part of the medical implant between the gingival tissue and the first recess. A flap of gingival tissue may be put back to its original position for this purpose and sutured for healing.

The method may comprise creating the first recess with a longitudinal extension, and wherein the creating the anchoring bore comprises creating the anchoring bore substantially in line with the longitudinal extension of the first recess. In an embodiment creating the anchoring bore is made by drilling a cylindrical bore with a bore diameter, bore length, and bore longitudinal orientation.

Preferably, the bore diameter is made in a dimension between that of the diameter of the apical end portion and the diameter of the apical (threaded portion) portion itself. The threads of the tapered apical portion may initially be easily introduced into the anchoring bore of the bone. The anchoring stability is then assured in accordance with a preferred method due to the larger diameter of the apical portion in relation to that of the bore when the implant is further introduced. The helical threads starting from the tapered portion thereof will assure during introduction of the implant in the bore that the implant may be tapped further down the hole. The tapering angle is defined in the drawings with the symbol a and is between 25 and 70 degrees.

Creating the first recess may in an embodiment be creating an indentation in the facial surface of the maxilla having a longitudinal extension, a maximum depth, and a maximum width. The maximum width is equal to or less than the bore diameter. The skull bone is in an embodiment the maxilla at a facial side of the skull of the patient at the indentation, and wherein the drilling a cylindrical bore is drilling the cylindrical bore in the maxilla at a zygomatic process, wherein the drilling the bore is made substantially aligned with the longitudinal extension of the indentation.

The anchoring may be made with an apical part of a medical implant having a larger diameter than the coronal portion thereof. Thus reliable anchoring is provided in a large anchoring bore. At the same time, a narrower coronal portion provides for several advantages. The first recess needs not be as large, i.e. the amount of bone tissue removed is limited. This is both patient friendly, and leaves sufficient remaining bone tissue of the maxilla such that mechanical strength thereof is not threatened. In addition, as the coronal portion takes less volume, potential irritation of surrounding tissue is minimized. Moreover, it is facilitated to implant a plurality of such medical implants in the narrow space available. Mechanical stability of the dental implant and precision of dental restorations attached thereto are maintained.

In an embodiment the skull bone is a zygomatic bone of a facial side of the skull of the patient at the indentation, and wherein the drilling a cylindrical bore is drilling the cylindrical bore in the zygomatic bone, wherein the drilling the bore is made substantially aligned with the longitudinal extension of the indentation. The first recess may be used as a guide channel for a drill when drilling the bore in the zygomatic bone, whereby the first recess in the outer surface of the maxilla is aligned with the bore in the zygomatic bone.

The method may further comprise using the first recess as a guide channel for a tool creating the anchoring bore, whereby aligning the anchoring bore with the first recess is provided. The anchoring bore may be s created along a line of sight from the first recess. Creating the anchoring bore may be made under full visibility, thus preventing damage of sensitive anatomical structures, such as nerves or blood vessels in the surgical working area of the medical procedure.

The facial bone tissue of the maxilla may be located on the external side of the maxilla adjacent to the alveolar ridge thereof.

Implanting the medical implant with the apical anchoring portion thereof may comprise bringing the apical anchoring portion into bone apposition in the anchoring bore. The coronal end portion of the medical implant may be brought into apposition to the bone tissue at the first recess. Thus, the first recess when implanted may support the medical implant.

As can be seen in the comparison shown in FIGS. 5A and 5B, a lever arm may be minimized and bending moments on the medical implant 20 may be minimized, compared to conventional implants 101. The minimization of bending moments is advantageous for long-term stability of the implant-supported dental restoration. The aligned implant according to some embodiments even allows for use of an aligned abutment.

The method may comprise marking a position of a bone entry site in the skull bone prior to creating the anchoring bore.

They may comprise positioning a non-threaded portion of the medical implant under a mucous membrane, prophylactically treating or preventing conditions such as catarrh or irritation of the mucous membrane.

Remaining teeth of the maxilla 512 of the patient may be extracted prior to the creating the first recess.

The method may comprise incising a gingiva of the maxilla 512 at an alveolar crest of the maxilla.

The method may comprise creating gingiva flaps interior and exterior of an alveolar crest of the maxilla; expanding the exterior gingiva flap from the alveolar crest of the maxilla to a zygomatic bone 510 of the patient adjoining the maxilla.

The inner gingiva flap may be temporary sutured temporary together in order to create a well visible surgical working area.

A substantially planar bone surface may be created at the alveolar crest of the maxilla by removing soft bone tissue for creating a bone foundation. Thereby a good basis for affixing dental restoration is provided.

Suturing the gingiva after the implanting concludes the medical procedure.

The medical implant applied in the medical procedure may be a medical implant according to embodiments described above.

In a specific embodiment, the method of implanting a medical implant in a patient comprises the following steps, wherein some of the steps may be made in another order or omitted in other embodiments:

610: extracting remaining teeth of a maxilla of the patient;
620: incising a gingiva of the maxilla;
630: creating gingiva flaps interior and exterior of an alveolar crest of the maxilla;
640: expanding the exterior gingiva flap from the maxilla to an os zygomaticus of the patient adjoining the maxilla;
650: temporary suturing inner gingiva flap together to create a line of sight;
660: removing still existing tooth fragments from the maxilla;
670: creating a substantially planar bone surface at the alveolar crest by removing soft bone tissue for creating a bone foundation;
680: marking a position of a drill hole entry in the os zygomaticus;
690: creating a recess in the maxilla external side that is aligned with the position of the drill hole entry in the os zygomaticus; the recess is created in the exterior bone surface of the maxilla, which is oriented towards the facial side of the maxilla; the recess is made to have a longitudinal extension oriented towards the zygomatic bone;
700: drilling a hole in the os zygomaticus from the position of the drill hole entry in the os zygomaticus, aligned with the recess; the recess may be used as a guide channel for a drill when drilling a bore in the zygomatic bone, whereby the recess in the outer surface of the maxilla is aligned with the bore in the zygomatic bone; the drilling operation is performed under full visibility, thus avoiding damage of sensitive anatomical structures such as nerves or blood vessels in the surgical working area of the medical procedure;

710: implanting a medical implant with an apical part into bone apposition in the drill hole, and positioning a coronal part of the medical implant at the recess; the unthreaded portion of the medical implant is positioned under the mucous membrane, thus avoiding catarrh or irritation of the mucous membrane; the mucous membrane may at least partly embed a rough surface of the unthreaded portion of the medical implant; and 720: the medical procedure is finalized by suturing the gingiva together, leaving the coronal end of the medical implant extending through the gingiva for fixation of abutments or dental restorations.

The medical implant may for instance be of the type described above with reference to FIGS. 2 and 3.

In a method of creating a dental restoration, the method of implanting a medical implant in a patient as described above is applied. Considering the position in space of the connection interface of the implant at the coronal end thereof, a dental restoration, such as a bridge is prepared. A plurality of medical implants may be provided in the patient. Subsequently the dental restoration is affixed to the connection interface of the at least one medical implant, at a coronal side thereof positioned at a alveolar crest of the maxilla.

A further advantage of the above-described method is that the patient does not need to have clinically symptom-free sinuses. Pre-surgical examination is facilitated. A wider range of patients may be treated.

Although embodiments of these inventions have been disclosed in the context of certain examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions.

What is claimed is:

1. A method of implanting a medical implant in a patient in a medical procedure, said method comprising:
   creating a recess along a surface of bone tissue located on an external side of a maxilla of said patient adjacent an alveolar ridge of said maxilla, said surface oriented toward a facial side of said maxilla, wherein said recess defines an indentation extending longitudinally along the surface and the recess does not extend into the maxillary sinus cavity;
   creating an anchoring bore externally in facial skull bone tissue at a distance from a location of said recess; and
   implanting said medical implant with an apical anchoring portion thereof including an apical end thereof in said anchoring bore, and positioning a non-threaded coronal part of said medical implant adjacent said recess, such that the medical implant does not extend into the maxillary sinus cavity.

2. The method of claim 1, comprising embedding said coronal part of said medical implant under gingival tissue.

3. The method according to claim 2, wherein said embedding comprises embedding said coronal part of said medical implant between said gingival tissue and said recess.

4. The method of claim 1, wherein said creating said anchoring bore comprises creating said anchoring bore substantially in line with said longitudinal extension of said recess.

5. The method of claim 1, further comprising marking a position of a bone entry site in said skull bone prior to creating said anchoring bore.

6. The method of claim 1, further comprising using said recess as a guide channel for a tool to create said anchoring bore such that said anchoring bore is aligned with said recess.

7. The method of claim 1, in which the anchoring bore is created along a line of sight from said recess.

8. The method of claim 1 comprising creating said anchoring bore under full visibility, thus preventing damage of sensitive anatomical structures.

9. The method of claim 1, in which said implanting said medical implant with said apical anchoring portion thereof comprises bringing said apical anchoring portion into bone apposition in said anchoring bore.

10. The method of claim 1, comprising positioning said non-threaded portion of said medical implant under a mucous membrane.

11. The method of claim 10, further comprising prophylactically treating or preventing conditions of the patient's mucous membrane.

12. The method of claim 1, comprising at least partly embedding a rough surface of said non-threaded portion of said medical implant under said mucous membrane.

13. A method of creating a dental restoration, comprising said method of claim 1, and further comprising the step of affixing a dental restoration to a connection interface of said medical implant at a coronal side thereof positioned at an alveolar crest of said maxilla.

14. The method of claim 1, wherein the facial skull bone tissue is zygomatic bone tissue.

15. A method of implanting a medical implant in a patient in a medical procedure, said method comprising:
   creating a recess on a surface of bone tissue located on an external side of a maxilla of said patient adjacent an alveolar ridge of said maxilla, said surface oriented toward a facial side of said maxilla, wherein said recess defines an indentation extending longitudinally along the surface and the recess does not extend into the maxillary sinus cavity;
   creatine an anchoring bore externally in zygomatic bone tissue at a distance from a location of said recess; and
   implanting said medical implant with an apical anchoring portion thereof including an apical end thereof in said anchoring bore, and positioning a non-threaded coronal part of said medical implant adjacent said recess, such that the medical implant does not extend into the maxillary sinus cavity,
   wherein the medical implant is anchored only in said zygomatic bone tissue.

16. The method of claim 1, wherein the medical implant is placed outside of the alveolar ridge of said maxilla.

* * * * *